(12) United States Patent
Jarret

(10) Patent No.: US 9,067,202 B1
(45) Date of Patent: Jun. 30, 2015

(54) SEMI-RIGID CULTURE VESSEL

(71) Applicant: Robert L. Jarret, Griffin, GA (US)

(72) Inventor: Robert L. Jarret, Griffin, GA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 13/626,253

(22) Filed: Sep. 25, 2012

(51) Int. Cl.
*B01L 1/00* (2006.01)
*B01L 3/00* (2006.01)

(52) U.S. Cl.
CPC .... *B01L 1/00* (2013.01); *B01L 3/00* (2013.01)

(58) Field of Classification Search
CPC ...................................... B01L 1/00; B01L 3/00
USPC ........... 435/283.1, 288.7, 289.1, 297.1, 304.1
See application file for complete search history.

(56) References Cited

U.S. PATENT DOCUMENTS

| | | | | |
|---|---|---|---|---|
| 4,285,998 A | * | 8/1981 | Thibodeau | 428/35.2 |
| 4,717,668 A | * | 1/1988 | Keilman et al. | 435/304.1 |
| 5,171,683 A | * | 12/1992 | Kertz | 435/297.1 |
| 6,551,819 B1 | * | 4/2003 | Simmet | 435/307.1 |
| 6,673,598 B1 | * | 1/2004 | Akers et al. | 435/298.2 |
| 2003/0168248 A1 | * | 9/2003 | Savoy et al. | 174/136 |
| 2007/0026516 A1 | * | 2/2007 | Martin et al. | 435/297.5 |
| 2007/0048859 A1 | * | 3/2007 | Sears | 435/289.1 |
| 2011/0258923 A1 | * | 10/2011 | Lais et al. | 428/99 |

* cited by examiner

*Primary Examiner* — Nathan Bowers
*Assistant Examiner* — Timothy Barlow
(74) *Attorney, Agent, or Firm* — Robert D. Jones; John D. Fado; Lesley Shaw

(57) ABSTRACT

The semi-rigid culture vessel is structured to transform a flexible culture vessel into a semi-rigid form to facilitate laboratory processes. The semi-rigid culture vessel includes at least two rims connected by at least one rib to form an internal support. The internal support is enclosed within the gas-permeable flexible culture vessel to form the semi-rigid culture vessel.

17 Claims, 4 Drawing Sheets

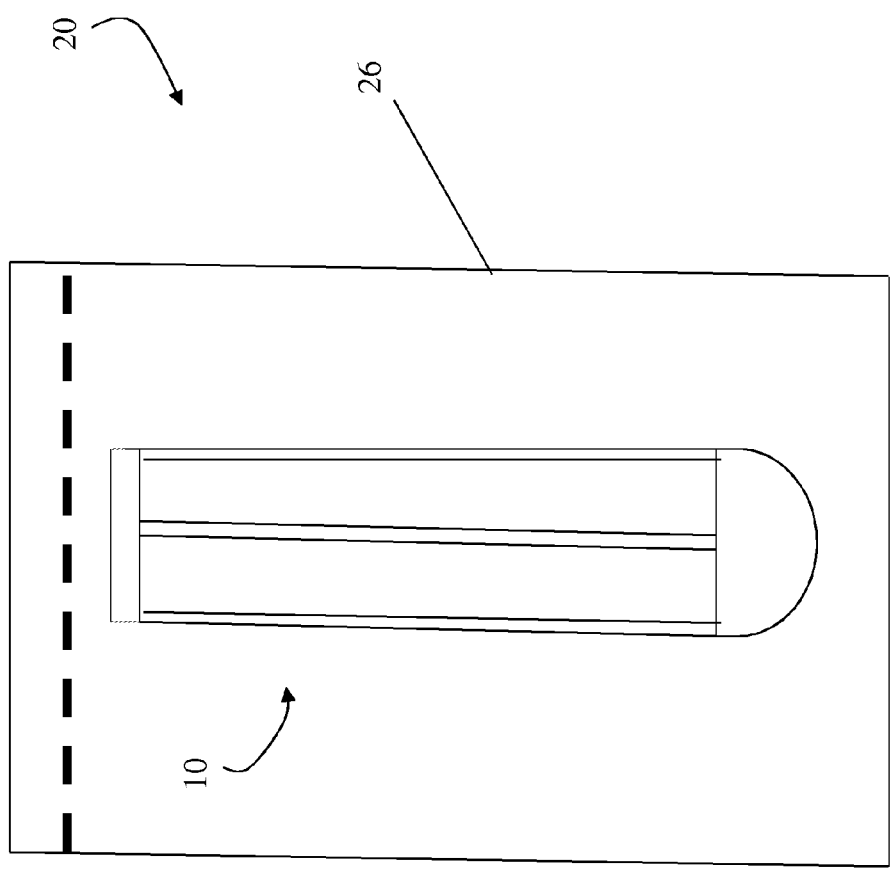

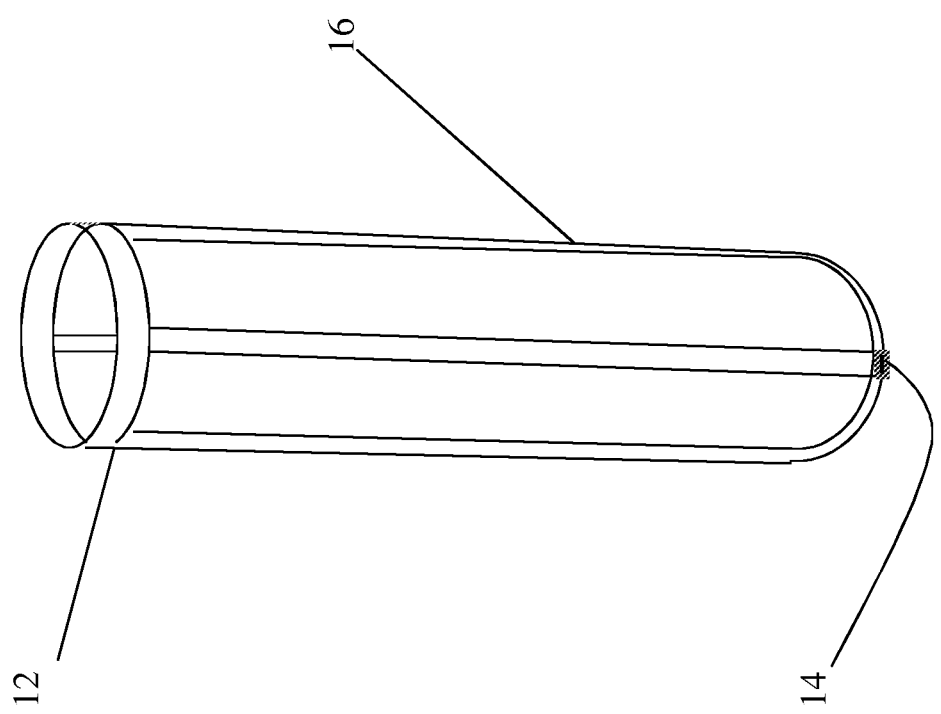

SEMI-RIGID CULTURE VESSEL

FIELD OF THE INVENTION

The present invention relates to an apparatus for preserving laboratory tissues. Specifically, the apparatus disclosed herein relates to a semi-rigid gas-permeable apparatus for the storage of various tissues and organisms.

BACKGROUND OF THE INVENTION

In the medical, veterinary, and horticultural areas, flexible culture vessels are the industry standard for storing living tissues. Flexible culture vessels (FCVs) are described (as "integuments") in U.S. Pat. No. 5,171,683 to Kertz titled INTEGUMENT AND METHOD FOR MICROPROPAGATION AND TISSUE CULTURING, which is herein incorporated by reference.

FCVs generally comprise gas permeable, heat sealable enclosures for in vitro micropropagation and maintenance of plants and the culture or maintenance of bacteria and fungi, eukarotic cell/tissues, and similar biological materials. FCVs are an efficient and cost-effective means of storing living tissues and provide a potentially useful alternative to jars, test tubes and plastic boxes. FCVs also resist contamination more effectively than traditional culture vessels (i.e. glass or hard plastic containers)—thus increasing the efficiency of the propagation/maintenance process.

However, FCVs are awkward to work with due to their lack of a defined shape. Unlike test tubes, jars, and other rigid storage vessels, FCVs cannot be readily stored in an upright position—which makes FCVs difficult to handle and impairs the ability of laboratory technicians to record data and inventory tissues stored or growing in the FCVs. Further, the conventional flat FCV configuration impairs the ability of light to uniformly penetrate into the FCVs and (in the case of plant tissues) inhibits the potential growth of materials cultured within the FCVs.

The need exists for a means of transforming FCVs so that the advantages of the gas-permeable, heat-sealable bags are retained while enabling the FCVs to be handled and monitored more effectively. The semi-rigid culture vessel described herein comprises a simple and inexpensive apparatus for transforming FCVs to enable an operator to store FCVs in an upright position while retaining the advantages of a flexible storage vessel.

SUMMARY OF THE INVENTION

This disclosure is directed to a semi-rigid culture vessel. The semi-rigid culture vessel comprises at least two rims connected by at least one rib to form an internal support. The internal support is enclosed within a gas-permeable flexible culture vessel to form the semi-rigid culture vessel.

This disclosure is also directed to a method of making a semi-rigid culture vessel. First and second rims are provided. The rims are connected by at least one rib to form an internal support. The internal support is deposited in a gas-permeable flexible culture vessel. The flexible culture vessel is then closed around the internal support to form the semi-rigid culture vessel.

BRIEF DESCRIPTION OF THE DRAWINGS

FIG. 3 is a profile view of the semi-rigid culture vessel.

FIG. 4 is an elevational view of an alternative embodiment of the FCV internal support apparatus.

DETAILED DESCRIPTION OF PREFERRED EMBODIMENTS

The apparatus described herein comprises a semi-rigid culture vessel. This disclosure also describes a method of making the semi-rigid culture vessel.

Figure 1:
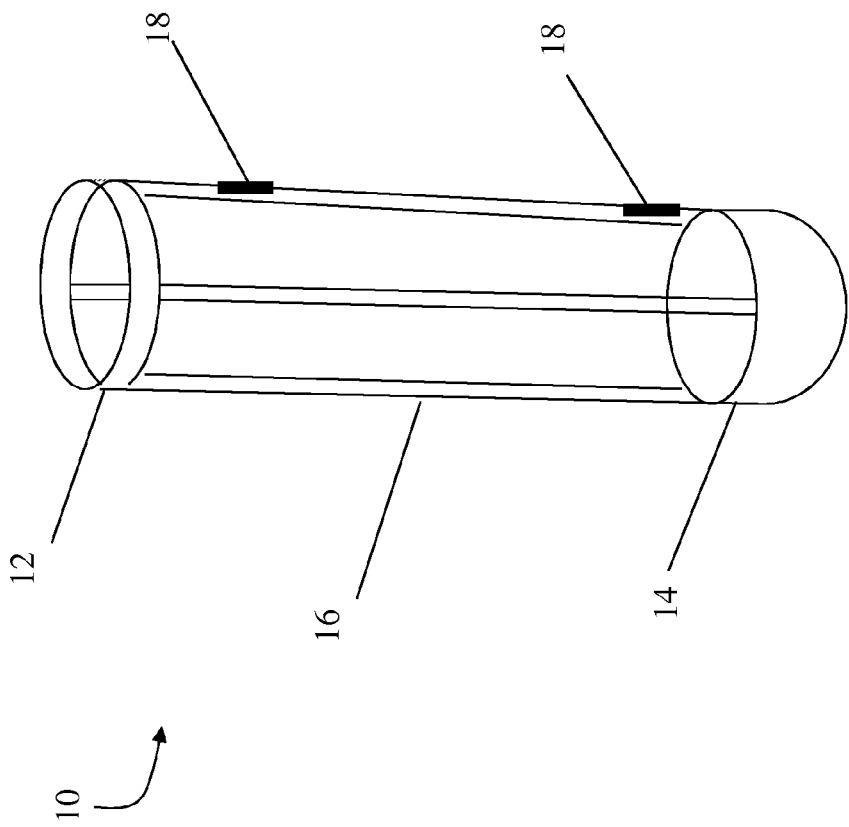
FIG. 1 is an elevational view of a FCV internal support apparatus.

FIG. 1 generally shows an FCV internal support 10. The internal support 10 comprises a first rim element 12 and a second rim element 14. The first 12 and second 14 rim elements are connected by at least one rib 16. The ribs 16 are designed to be spaced sufficiently far apart so as not to obscure or substantially interfere with any matter within or light transmittance into the internal support 10, but structurally robust enough to provide a semi-rigid form.

Figure 2:
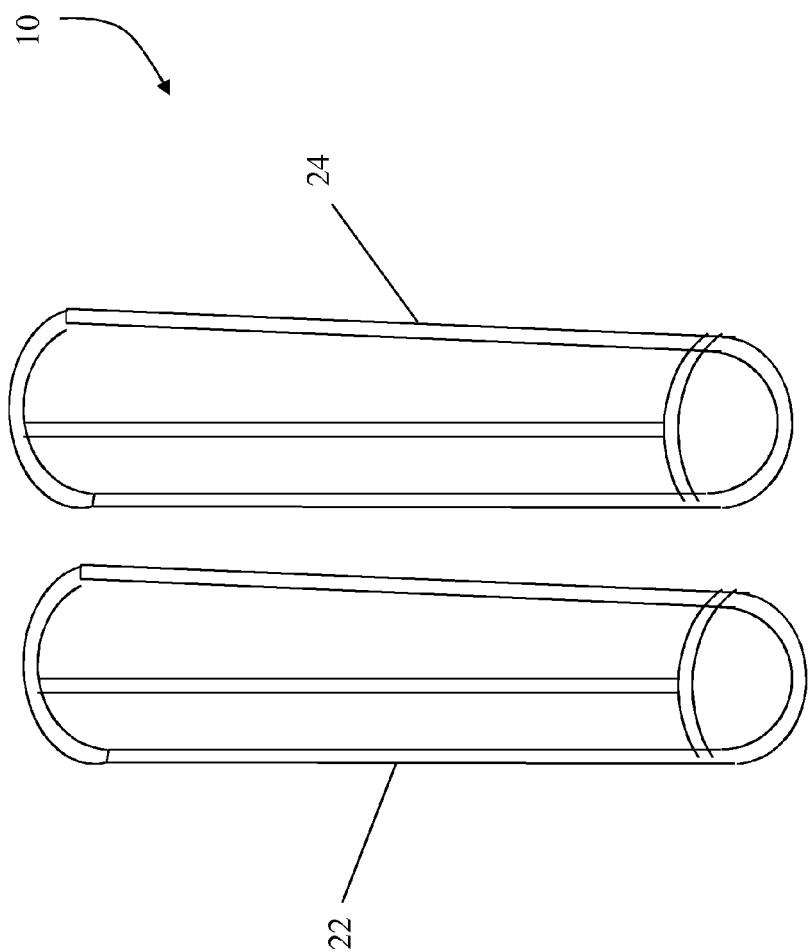
FIG. 2 is an elevational view of the two halves of the FCV internal support apparatus.

As best shown in FIG. 2, in the preferred embodiment, the FCV internal support 10 is essentially comprised of two mirror image halves 22, 24. As shown in FIG. 1, the halves 22, 24 are connected by hinges 18 that enable the internal support to open and close. The FCV internal support 10 generally has a cylindrical shape with the first rim element 12 defining a circumference of a circle, and the second rim element 14 having an internally concave (hollow) shape.

As best shown in FIG. 3, the ribs 16 are linear and, in combination with the rims 12, 14, define an open space that provides the sealed FCV 26 with a semi-rigid form. For the purposes of this disclosure, a "semi-rigid culture vessel" 20 comprises an internal support 10 enclosed within an FCV 26. An enlarged and modified test tube rack (not shown) easily enables a sealed FCV 26 with an enclosed internal support 10 to be stored in an upright position.

In alternative embodiments, the rims 12, 14, may have alternative geometric and non-geometric shapes. For example, the rims 12, 14 may have a generally triangular, rectangular, or octagonal shape. The rims 12, 13 may also be non-symmetric. As shown in FIG. 4, for the purposes of this disclosure, one or both of the "rims" 12, 14 may simply comprise a solid intersecting portion of the ribs 16. The ribs 16 may be helical or have other non-linear forms.

Further, in alternative embodiments, there may be as few as one rim 12 and as few as one rib 16, or there may be multiple rims 12, 14, and ribs 16. Essentially, the rims 12, 14 and ribs 16 may have any form known in the art consistent with providing an open space in the interior of the FCV.

Although the preferred embodiment comprises two halves 22, 24 of an internal support 10 connected by hinges 18 (as shown in FIG. 1), the internal support 10 may only comprise a single unitary (non-hinged) body (for example a cylinder or cube). The internal support 10 may also comprise two unconnected halves 22, 24 that snap or otherwise connect together (as shown in FIG. 2). Further, the internal support 10 may comprise more than two pieces and the pieces of the support 10 may be connected by any means known in the art.

The invention disclosed herein is also directed to a method of making a semi-rigid culture vessel. The method comprises providing first and second rims 12, 14, and connecting the rims 12, 14 with at least one rib 16 to construct an internal support 10. The internal support 10 is then enclosed in an FCV so that the assembly forms a semi-rigid culture vessel.

For the foregoing reasons, it is clear that the apparatus described herein provides an innovative semi-rigid culture vessel and a method of making a semi-rigid culture vessel.

The apparatus and method may be modified in multiple ways and applied in various technological applications. The method and apparatus may be modified and customized as required by a specific operation or application, and the individual components may be modified and defined, as required, to achieve the desired result.

Although the materials of construction are not described, they may include a variety of compositions consistent with the function of the invention. However, in the preferred embodiment, the materials of construction must enable the semi-rigid culture vessel to be autoclaved. Variations in the materials of construction are not to be regarded as a departure from the spirit and scope of the invention, and all such modifications as would be obvious to one skilled in the art are intended to be included within the scope of the following claims.

What is claimed is:

1. A semi-rigid culture vessel comprising:
   at least first and second rims;
   at least one rib connecting the first rim with the second rim to form a non-collapsible semi-rigid internal support; and,
   a flexible culture vessel consisting of an integument having a membrane that is gas-permeable but impermeable to liquid and microorganisms, the integument consisting of a high density polyethylene material which is pliable and collapsible such that the polyethylene material can be stored and shipped in rolls, the polyethylene material being capable of sterilization in an autoclave;
   whereby the internal support is completely enclosed within the flexible culture vessel to form the semi-rigid culture vessel, the semi-rigid internal support being sufficiently structurally robust to enable the flexible culture vessel to be stored in an upright position.

2. The semi-rigid culture vessel of claim 1 wherein the internal support is sealed within the flexible culture vessel.

3. The semi-rigid culture vessel of claim 1 wherein the internal support is heat-sealed within the flexible culture vessel.

4. The semi-rigid culture vessel of claim 1 wherein the flexible culture vessel is at least partially transparent.

5. The semi-rigid culture vessel of claim 1 wherein the semi-rigid culture vessel is structured and supported internally by the internal support so that the semi-rigid culture vessel is storable in essentially an upright vertical position.

6. The semi-rigid culture vessel of claim 1 comprising four ribs.

7. The semi-rigid culture vessel of claim 1 wherein the internal support comprises a plurality of ribs.

8. The semi-rigid culture vessel of claim 1 wherein the in the internal support comprises more than two rims.

9. The semi-rigid culture vessel of claim 1 wherein the internal support comprises a single unitary body.

10. The semi-rigid culture vessel of claim 1 wherein the internal support comprises at least two connectable sections.

11. The semi-rigid culture vessel of claim 1 wherein the internal support comprises two sections hinged together so that the two sections are joinable to form a cylindrical internal support.

12. The semi-rigid culture vessel of claim 1 wherein the first rim defines a circumference of a circle.

13. The semi-rigid culture vessel of claim 1 wherein the second rim further comprises a cup element.

14. The semi-rigid culture vessel of claim 1 wherein the second rim comprises an intersecting portion of the ribs.

15. A method of making a semi-rigid culture vessel, the method comprising the steps of:
   (a) providing a first rim;
   (b) providing a second rim parallel with the first rim;
   (c) providing at least one rib and connecting the first rim with the second rim to form a non-collapsible semi-rigid internal support;
   (d) depositing the internal support in a flexible culture vessel consisting of an integument having a membrane that is gas-permeable but impermeable to liquid and microorganisms, the integument consisting of a high density polyethylene material which is pliable and collapsible such that the polyethylene material can be stored and shipped in rolls, the polyethylene material being capable of sterilization in an autoclave, the semi-rigid internal support being sufficiently structurally robust to enable the flexible culture vessel to be stored in an upright position; and
   (e) closing the flexible culture vessel.

16. The method of claim 15 further comprising:
   (f) sealing the flexible culture vessel.

17. The method of claim 15 further comprising:
   (f) heat-sealing the flexible culture vessel.

* * * * *